(12) United States Patent
Virtanen et al.

(10) Patent No.: US 10,429,371 B2
(45) Date of Patent: Oct. 1, 2019

(54) METHOD AND SYSTEM FOR EXTRACTING GAS OR GAS MIXTURES FROM A LIQUID FOR PERFORMING DISSOLVED GAS OR GAS MIXTURE ANALYSIS

(71) Applicant: VAISALA OYJ, Helsinki, FL (US)

(72) Inventors: Sami Virtanen, Helsinki, FL (US); Veli-Pekka Viitanen, Helsinki, FL (US)

(73) Assignee: Vaisala Oyj, Vantaa (FI)

( * ) Notice: Subject to any disclaimer, the term of this patent is extended or adjusted under 35 U.S.C. 154(b) by 75 days.

(21) Appl. No.: 15/328,526

(22) PCT Filed: Aug. 11, 2015

(86) PCT No.: PCT/FI2015/050521
§ 371 (c)(1),
(2) Date: Jan. 24, 2017

(87) PCT Pub. No.: WO2016/027003
PCT Pub. Date: Feb. 25, 2016

(65) Prior Publication Data
US 2017/0212093 A1    Jul. 27, 2017

(30) Foreign Application Priority Data
Aug. 18, 2014 (FI) ..................... 20145729

(51) Int. Cl.
*G01N 33/28* (2006.01)
*B01D 19/00* (2006.01)
(Continued)

(52) U.S. Cl.
CPC ..... *G01N 33/2841* (2013.01); *B01D 19/0036* (2013.01); *B01D 19/0063* (2013.01);
(Continued)

(58) Field of Classification Search
None
See application file for complete search history.

(56) References Cited

U.S. PATENT DOCUMENTS 3,844,160 A    10/1974  Yamaoka
4,763,514 A  *  8/1988  Naito ................. G01N 33/2841
                                                  73/19.01
(Continued)

FOREIGN PATENT DOCUMENTS

GB    2129437 A    5/1984
JP    S53117713 A    10/1978
(Continued)

*Primary Examiner* — Paul M. West
*Assistant Examiner* — Mark A Shabman
(74) *Attorney, Agent, or Firm* — Seppo Laine Oy (57) ABSTRACT

The present invention concerns a system (1) for extracting gas or gas mixtures from a liquid for performing dissolved gas or gas mixture analysis, the system (1) comprising a container (2) for storing a liquid and/or a gas or gas mixture, a liquid pump (3) which is connected to the container (2), a means for feeding the system (1) with a liquid and emptying the system (1) of the liquid, a gas analyzer which is connected to the container (2), and a piping (14) which is connected to the container (2), and wherein the piping (14), the liquid pump (3) and the container (2) are configured to circulate the liquid. The invention also concerns a method for extracting gas or gas mixtures from a liquid for performing dissolved gas or gas mixture analysis.

15 Claims, 9 Drawing Sheets

(51) Int. Cl.
    *B01F 3/04*     (2006.01)
    *B01F 5/10*     (2006.01)
    *G01R 31/02*    (2006.01)
(52) U.S. Cl.
    CPC .......... *B01F 3/04503* (2013.01); *B01F 5/102* (2013.01); *B01F 2215/0037* (2013.01); *G01R 31/027* (2013.01)

(56) References Cited

U.S. PATENT DOCUMENTS

| | | | | |
|---|---|---|---|---|
| 5,965,805 | A * | 10/1999 | Watts | G01N 7/14 |
| | | | | 73/19.11 |
| 6,393,893 | B1 * | 5/2002 | Fetz | B29B 7/286 |
| | | | | 73/19.01 |
| 6,443,001 | B1 | 9/2002 | Duriez et al. | |
| 7,040,138 | B2 * | 5/2006 | Braesel | G01N 33/2841 |
| | | | | 73/19.01 |
| 8,075,675 | B2 * | 12/2011 | Mahoney | B01D 19/0031 |
| | | | | 95/46 |
| 2003/0172716 | A1 | 9/2003 | Braesel et al. | |

FOREIGN PATENT DOCUMENTS

| | | |
|---|---|---|
| JP | S60253840 A | 12/1985 |
| JP | 2004022692 A | 1/2004 |
| WO | WO0195990 A1 | 12/2001 |

\* cited by examiner

METHOD AND SYSTEM FOR EXTRACTING GAS OR GAS MIXTURES FROM A LIQUID FOR PERFORMING DISSOLVED GAS OR GAS MIXTURE ANALYSIS

TECHNICAL FIELD OF THE INVENTION

The present invention relates to a method for extracting gas or gas mixtures from a liquid for performing dissolved gas or gas mixture analysis. The present invention further relates to a system for extracting gas or gas mixtures from a liquid for performing dissolved gas or gas mixture analysis. The present invention furthermore relates to a computer readable medium having stored thereon a set of computer implementable instructions.

BACKGROUND OF THE INVENTION

Analysis of gases dissolved in liquids is a common technological challenge in monitoring the gas content, for example of oil and water, in industrial and environmental applications. An important example is the condition monitoring of large power transformers, which is mainly based on transformer oil dissolved gas analysis.

The document "Oil-filled electrical equipment—Sampling of gases and analysis of free and dissolved gases—Guidance, International Electrical Commission, International Standard, Edition 4.0 (2011), ISBN 978-2-88912-768-9" deals, for example, with techniques for sampling gases from gas collecting relays from power transformers.

Currently available devices for on-line measurement of gases or gas mixtures dissolved in oil contained by electric power transformers and their load tap changers typically use the so-called headspace sampling method or sample the dissolved gases or gas mixtures through semipermeable membranes. The headspace sampling method is inherently rather inaccurate way to measure dissolved gas contents, because of variation in the solubility coefficients for example between different species of oil. Same applies to methods utilizing semipermeable membranes which are also plagued by contamination problems. The high-end on-line devices use vacuum extraction sampling, but incorporate complicated technology, for example vacuum pumps, and are consequently expensive.

The Finnish patent application 20135951 further describes a method and system for gas concentration measurement of gas or gas mixtures dissolved in liquids. A gas or gas mixture dissolved in a liquid sample is extracted from the liquid sample using an extraction system and conducted into a measurement chamber. Then a measurement signal is generated by means of a radiant source and the measurement signal is directed to a measurement object in a measurement chamber containing the gas or gas mixture to be measured. The measurement signal is filtered using at least two wavelengths, whereupon the filtering is preferably implemented by means of an electrically tunable, short-resonator Fabry-Perot interferometer. Then the filtered measurement signals are detected my means of a detector.

Additionally, document EP 1950560 A1 discloses a method which involves filling a separation vessel with transformer oil, such that a gas chamber remains above the transformer oil in the separation vessel. A measuring chamber is filled with gas from the gas space above the transformer oil. A concentration of a gas component is measured in the measuring chamber with the help of sensor devices, particularly arranged in the measuring chamber. The sensor devices measure the concentration of one or multiple gas components selected from dihydrogen, carbon monoxide, ethylene and acetylene. The document also teaches a device for quantitative analysis of gases in a transformer oil.

Document U.S. Pat. No. 6,443,001 B1 teaches an extraction, analysis and measuring method and system intended for constituents carried along by a well fluid during drilling operations. The volume of drilling fluid contained in a vessel is subjected to stirring in order to favour extraction through degasing and evaporation. The stirring operation may take place by means of a rotating agitator. The measuring means comprises an expensive vacuum pump in order to create an underpressure that can reach several millibars.

Document JP 560253840 A discloses a method to prevent the penetration of dissolved gas into an oil immersed electric machinery tank. A bellows is used in order to provide a space in a gas extraction chamber. Air is flowed into the space and a gaseous mixture is guided to a detection chamber.

SUMMARY OF THE INVENTION

An object of certain embodiments of the present invention is to provide a method for extracting gas or gas mixtures from a liquid for performing dissolved gas or gas mixture analysis. A further object of certain embodiments of the present invention is to provide a system for extracting gas or gas mixtures from a liquid for performing dissolved gas or gas mixture analysis. Furthermore, an object of certain embodiments of the present invention is to provide a computer readable medium having stored thereon a set of computer implementable instructions.

The method and system according to certain embodiments of the present invention are especially intended to be used for on-line measurements of gas or gas mixtures dissolved in oil contained by electric power transformers and their load tap changers.

These and other objects are achieved by the embodiments of the present invention, as hereinafter described and claimed. According to an aspect of the invention, there is provided a system for extracting gas or gas mixtures from a liquid for performing dissolved gas or gas mixture analysis, the system comprising a container for storing a liquid and/or a gas or gas mixture, a liquid pump which is connected to the container, a means for feeding the system with a liquid and emptying the system of the liquid, a gas analyzer which is connected to the container, and a piping which is connected to the container, and wherein the piping, the liquid pump and the container are configured to circulate the liquid.

According to a certain embodiment, the liquid pump is configured to reverse a liquid flow direction. According to another certain embodiment, the system comprises a means for reversing the liquid flow direction.

In an embodiment, the system includes a pressure sensor which is connected to the container, the piping, and/or a measurement chamber of the gas analyzer.

In an embodiment, the system includes means for measuring a liquid level in the container. In another embodiment, the means for feeding the system with a liquid and emptying the system of the liquid comprises an inlet/outlet piping. According to an embodiment, the inlet/outlet piping is connected to a first three-way valve which is connected to the liquid pump and the piping.

In an embodiment, the system includes a second three-way valve which is connected to the container, the piping and the gas analyzer. In another embodiment, the system includes a valve configured to remove air out of the system.

According to an embodiment, the container includes a first opening essentially on top of the container and a second opening essentially at the bottom of the container.

According to another embodiment, the liquid pump is hermetically sealed.

In an embodiment, a gas/liquid inlet member on top of the container is configured to simultaneously suck in both gas and liquid, if the liquid is near a suction member. In a certain embodiment, the cross sectional area of the gas/liquid inlet member is less than 50% of the cross sectional area of the piping connected to the gas/liquid inlet member.

In another embodiment, the system comprises a device for stirring the liquid mechanically.

According to an embodiment, the system comprises a means for controlling the temperature of the liquid in the container.

According to another aspect, the object of embodiments of the invention can be also achieved by a method for extracting gas or a gas mixture from a liquid for performing dissolved gas or gas mixture analysis, the method comprising the steps of:

extracting the gas or gas mixture from the liquid utilizing mechanical agitation and pressure substantially reduced from ambient pressure, transferring the extracted gas or gas mixture into a gas analyzer, and dissolving the gas or gas mixture back into the liquid.

According to an embodiment, the gas or gas mixture is transferred into the gas analyzer by elevating a liquid level.

In an embodiment, a gas pressure or gas mixture pressure is varied between successive measurements by the gas analyzer after transferring the extracted gas or gas mixture into the gas analyzer and measuring a gas or gas mixture concentration. In a certain embodiment, the gas pressure or gas mixture pressure is varied by elevating or lowering a liquid level.

According to an embodiment, the gas or gas mixture is extracted by circulating the liquid from the bottom of the container to the top of the container, while the top of the container contains gas or gas mixture at a pressure typically less than 0.5 bar, normally less than 0.3 bar, and preferably less than 0.2 bar.

In an embodiment, the gas or gas mixture is dissolved back into the liquid by circulating the liquid/gas mixture from the top of the container to the bottom of the container or from the bottom of the container to the top of the container.

According to an embodiment, the liquid pump is used while the liquid level is elevated or lowered in order to vary the pressure without unwanted gas extraction.

According to another embodiment, the liquid pump is stopped and the flow is driven with hydrostatic pressure while the liquid level is elevated in order to vary the pressure without unwanted gas extraction.

According to a further aspect of the invention, there is provided a computer readable medium having stored thereon a set of computer implementable instructions capable of causing a processor, in connection with the system according to any one of claims 1 to 14, to calculate a gas or gas mixture content dissolved in a liquid sample.

Considerable advantages are obtained by means of the embodiments of the present invention. A method and system for extracting gas or gas mixtures from a liquid for performing dissolved gas or gas mixture analysis are provided by means of the embodiments of the present invention.

The method and system according to certain embodiments of the present invention enable a high-degree extraction comparable to high-end vacuum extraction methods and systems. The provided system is technologically simple and cost effective. The system does not include an expensive vacuum pump needing maintenance that vacuum gas extraction devices typically have. There are further no semipermeable membranes in the system included that are prone to contamination. Furthermore, the system does not require bellows in connection with a linear motor. The system is capable of being manufactured simply, cost effectively, and in industrial scale. The system is more compact and has less weight due to a reduced number of components.

Additionally, the inherent ability to measure the extracted gas at various pressures facilitates offset compensation by pressure variation, when using an IR absorption measurement method. This possibility essentially improves the measurement accuracy and the stability and enables very long calibration intervals without any human intervention. The inherent ability to measure the gas at various pressures can be utilized to extend the dynamics of the gas concentration measurement. The measurement range can be extended by a factor in the order of 10 compared to the range provided by the gas measurement device itself depending on the relative volumes of the liquid container, the liquid sample, and the gas measurement chamber.

The system is also able to compress the extracted gas, thus improving the detection limit and the measurement accuracy. Further, the number of mechanically moving and load-bearing parts is very limited and the installation of the system is easy and can be quickly done.

According to an embodiment, air can be pushed out of the system via the valve. In another embodiment, an external vacuum pump can be used to speed up the process. Therefore, the liquid is not exposed to additional moisture and oxygen from ambient air, thus efficiently improving the gas or gas mixture concentration measurement result. It is also not necessary to push the dissolved gas or gas mixture into the measurement chamber by means of an inert gas or air. Measurement results are improved due to transferring the gas or gas mixture into the measurement chamber by means of raising the liquid level.

Due to the system's low mass, the device can be easily attached to a power transformer according to certain embodiments, for example, using only the inlet/outlet piping connection. An additional mounting bracket or long piping is not required. The system can be connected to the liquid source containing liquid to be analyzed by a single pipe. The system is further hermetically isolated from ambient air, thus increasing the reliability of the system. Furthermore, the liquid sample can be returned into the liquid source, while having the same gas or gas mixture concentration which it had before feeding the system with the liquid sample.

The system according to the embodiments of the invention does not require recalibration, is maintenance free and does not need changing of gas bottles as similar devices typically do.

The construction of the system provides a sufficient liquid column height between the pump inlet and the lowest liquid surface level, thus guaranteeing the hydrostatic pressure at the pump inlet, which effectively prevents pump cavitation or reduces the risk of cavitation that could lead to unwanted gas formation.

BRIEF DESCRIPTION OF THE DRAWINGS

For a more complete understanding of particular embodiments of the present invention and their advantages, reference is now made to the following descriptions, taken in conjunction with the accompanying drawings. In the drawings.

DETAILED DESCRIPTION OF EMBODIMENTS OF THE INVENTION

Figure 1:
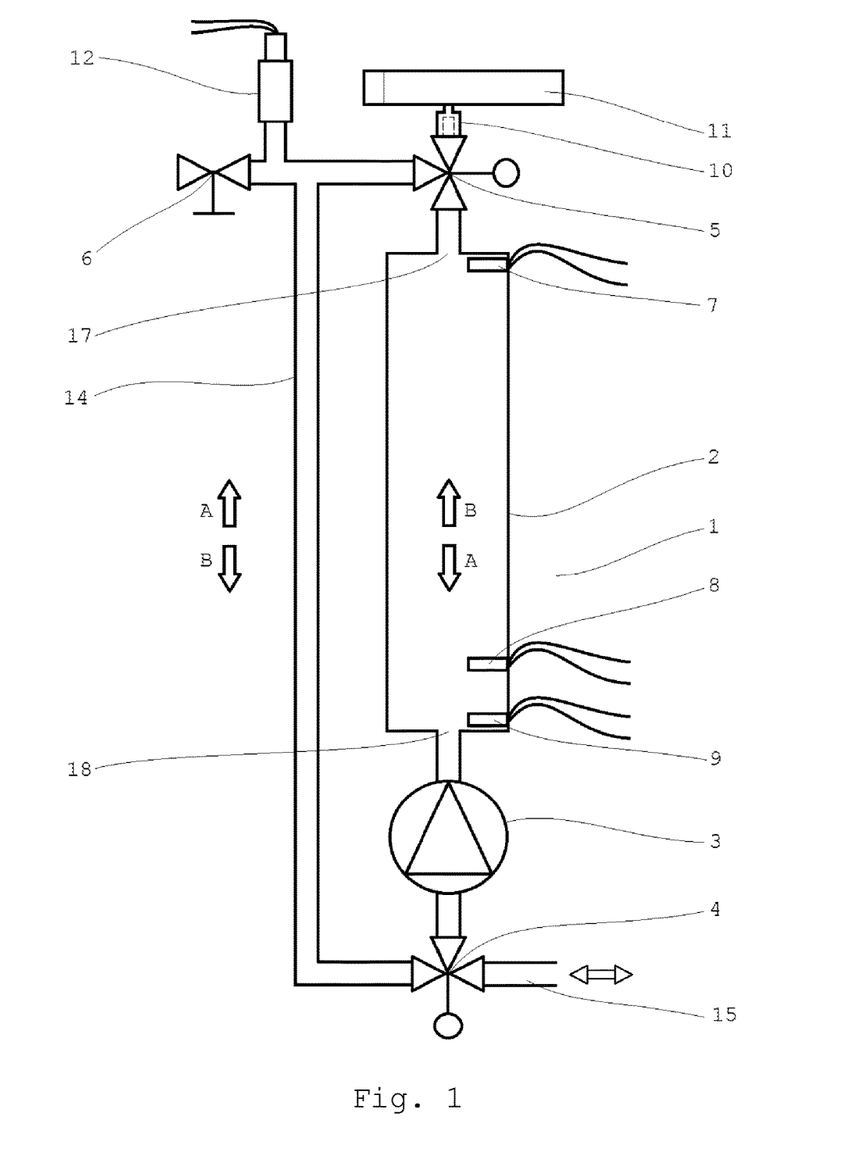
FIG. 1 illustrates a schematic view of a system according to a first embodiment of the present invention.

In FIG. 1 a schematic view of a system according to a first embodiment of the present invention is illustrated. The system 1 includes a container 2, which is connected to a two-way liquid pump 3 at one end, which pump 3 is connected to a first three-way valve 4. The liquid pump 3 is a bidirectional pump with an adjustable pumping rate. The container 2 is further connected to a second three-way valve 5 at the other end. The second three way valve 5 is in one direction connected to a gas/liquid separation vessel 10, which is connected to a measurement chamber, and in the other direction the second three-way valve is connected to the first three-way valve 4, a valve 6, and a pressure sensor 12 via piping 14. The gas/liquid separation vessel 10 is configured in such a way that liquid, droplets, and/or aerosol cannot pass the gas/liquid separation vessel 10 and only gas or gas mixture is allowed to enter the measurement chamber 11. The gas measurement chamber 11 may be, for example, an IR gas measurement chamber. The first three-way valve 4 is further connected to an inlet/outlet piping 15. The container 2 furthermore includes a first liquid level sensor 7, a second liquid level sensor 8, and a third liquid level sensor 9. According to a certain embodiment, the system may include a single device for continuously measuring any liquid level in the container 2, which device is not shown in FIG. 1. The aforementioned device may be based on an optical, mechanical or acoustical liquid level measurement technique, for instance. The system 1 is vacuum tight.

Initially, when installed, inlet/outlet piping 15 is connected to a liquid source, for example a liquid vessel, containing the liquid to be analyzed. Then the first three-way valve 4 is opened towards piping 14 and air is removed via the valve 6 using an external vacuum pump, which is not shown in FIG. 1. Alternatively, the system 1 can be filled with a liquid by opening the first three-way valve 4 towards inlet/outlet piping 15, pumping the liquid slowly to fill the container 1, and simultaneously letting air out of the system 1 via the valve 6. The valve 6 is only used during commissioning of the system 1 and may be, for example, a manual valve or a magnetic valve.

The extraction-measurement-cycle is started by opening the first three-way valve 4 towards the inlet piping 14 and closing the second three-way valve 5 towards the measurement chamber 11, and pumping liquid with the two-way liquid pump 3 such that gas extraction is minimized at this stage. Pumping of the liquid typically takes place with slow speed. The liquid speed in the tubing may be, for example, in the range between 0.1 [m/s] and 0.2 [m/s], 0.1 [m/s] and 0.3 [m/s], or 0.1 [m/s] and 0.5 [m/s]. Liquid is fed into the system 1 until the container 2 and the piping 15 are filled as completely as possible and the pressure sensor 12 shows overpressure. Typically liquid is filled into the system 1 until a pressure in the range between 1.2 [bar] and 2.0 [bar] is reached. The first three-way valve 4 is then opened towards the piping 14 and the liquid is circulated by pumping it with the two-way liquid pump 3 until some of the gas present in the system 1 is dissolved into the liquid and pressure is lowered. Pumping of the liquid typically takes place with high speed at this stage. The liquid speed in the tubing may be, for example, in the range between 1.0 [m/s] and 8.0 [m/s], with even higher speeds at the suction member. Then additional liquid from the inlet/outlet piping 15 can be pumped into the system 1 and the cycle is repeated until there is practically no free gas phase in the container 2, the piping 14 and the liquid pump 3. If the two-way liquid pump can operate when there are gas bubbles in the stream through it, and if there is not too much gas present in the system 1, pumping is advantageously done in the direction of the arrows B instead of A. This helps breaking up gas bubbles and can substantially increase the dissolving rate.

When the system 1 is filled with liquid, the first three-way valve 4 is opened towards the inlet/outlet piping 15 and liquid is pumped out of the system 1 until its level reaches the second liquid level sensor 8. During pumping, typically only a very small amount of gas is extracted from the liquid, and pressure is decreased to a very low level. The pressure may be, for example, in the range between 0.01 [bar] and 0.1 [bar]. The remaining liquid between the first three-way valve 4 and the second liquid level sensor 8 is the liquid sample from which a gas or gas mixture is to be extracted and analyzed. The first three-way valve 4 is now opened towards the piping 14 and the extraction phase starts by circulating the liquid with the two-way liquid pump 3 in the direction of arrows A. The pumping of the liquid typically takes place with high speed. The liquid speed in the tubing may be, for example, in the range between 1.0 [m/s] and 8.0 [m/s], or greater than ten times the pumping speed during the oil inlet phase. The mechanical disturbance on the liquid and the low pressure extracts the dissolved gas or gas mixture effectively from the liquid.

The liquid pump 3 is located in vertical direction under the container 2, i.e. below the level of the bottom of the container 2. The position of the liquid pump 3 is typically at the bottom of or as close as possible to the bottom of the system 1 in order to provide sufficient pressure and to reduce the risk of cavitation which can harm the measurement accuracy. The hydrostatic pressure at the position of the liquid pump 3 is sufficient due to the liquid column above the liquid pump 3. The distance between the inlet of the liquid pump 3 and the second level sensor 8 may be, for example, in the range between 0.2 [m] and 0.3 [m]. The cross sectional area of the piping between the container 2 and the liquid pump 3 is optimized such that the flow resistance is sufficiently low. This can be realized by increasing the cross sectional area of the piping between the container 2 and the liquid pump 3 compared to the cross sectional area of the piping in other parts of the system 1.

According to certain embodiments, the cross sectional area of the piping between the container 2 and the liquid pump 3 is the system's greatest piping cross sectional area.

After the gas or gas mixture extraction rate has been slowed down and pressure increase saturated, the first three-way valve 4 is opened towards the inlet/outlet piping 15, the second three-way valve 5 is opened towards the measurement chamber 11, and the direction of the two-way liquid pump 3 is reversed. The pumping rate is advantageously kept slow to avoid gas or gas mixture extraction from the incoming liquid. At this stage, the pumping speed may be, for example, below 0.2 [m/s]. According to other embodiments, the two-way liquid pump 3 is stopped at this stage, if the bypass flow is sufficient.

The raising liquid level pushes the extracted gas or gas mixture sample into the measurement chamber 11. Pumping is typically stopped when the liquid level reaches the first liquid level sensor 7. The second three-way valve 5 is closed towards the measurement chamber 11 and the gas measurement is performed. The gas measurement method may be, for example, an IR transmittance measurement.

Pressure is reduced after the first measurement by pumping oil out of the system 1. Then the IR transmittance of the sample gas is measured at very low pressure. The pressure may be, for example, in the range between 0.01 [bar] and 0.1 [bar]. With the help of the system 1 capable of generating a pressure difference of, for example 1 [bar] or more, a number of accurate pressure levels can be generated. The ability to measure the gas or gas mixture sample at different pressures gives the possibility to cancel the effects of various slow drift mechanisms on the results. As a result a substantially better measurement accuracy and stability is achieved.

After the gas or gas mixture measurement, the second three-way valve 5 is again opened towards the measurement chamber 11 and liquid is pumped out of the container 2 until its level reaches the third liquid level sensor 9. This transfers the majority of the measured gas or gas mixture sample into the container 2. The volume of the container 2 is typically much larger than the volume of the measurement chamber 11. Then the second three-way valve 5 is again closed towards the measurement chamber 11 and the gas is again dissolved in the liquid by feeding liquid into the system 1 until the container 2 and the piping 15 are filled as completely as possible and the pressure sensor 12 shows overpressure. At this stage, the pressure may be, for example, 1.5 [bar]. The first three-way valve 4 is then opened towards the piping 14 and the liquid is circulated by pumping it with the two-way liquid pump 3 until some of the gas present in the system 1 is dissolved into the liquid and pressure is lowered. Then additional liquid from the inlet/outlet piping 15 can be pumped into the system 1 and the cycle is repeated until there is practically no free gas phase in the container 2, the piping 14 and the liquid pump 3. The gas transfer and dissolving cycles can be repeated to evacuate the measurement chamber 11 more accurately.

After measuring the IR transmittance of the gas or gas mixture sample at low pressure, the system is ready for the next extraction/measurement cycle.

Figure 2:
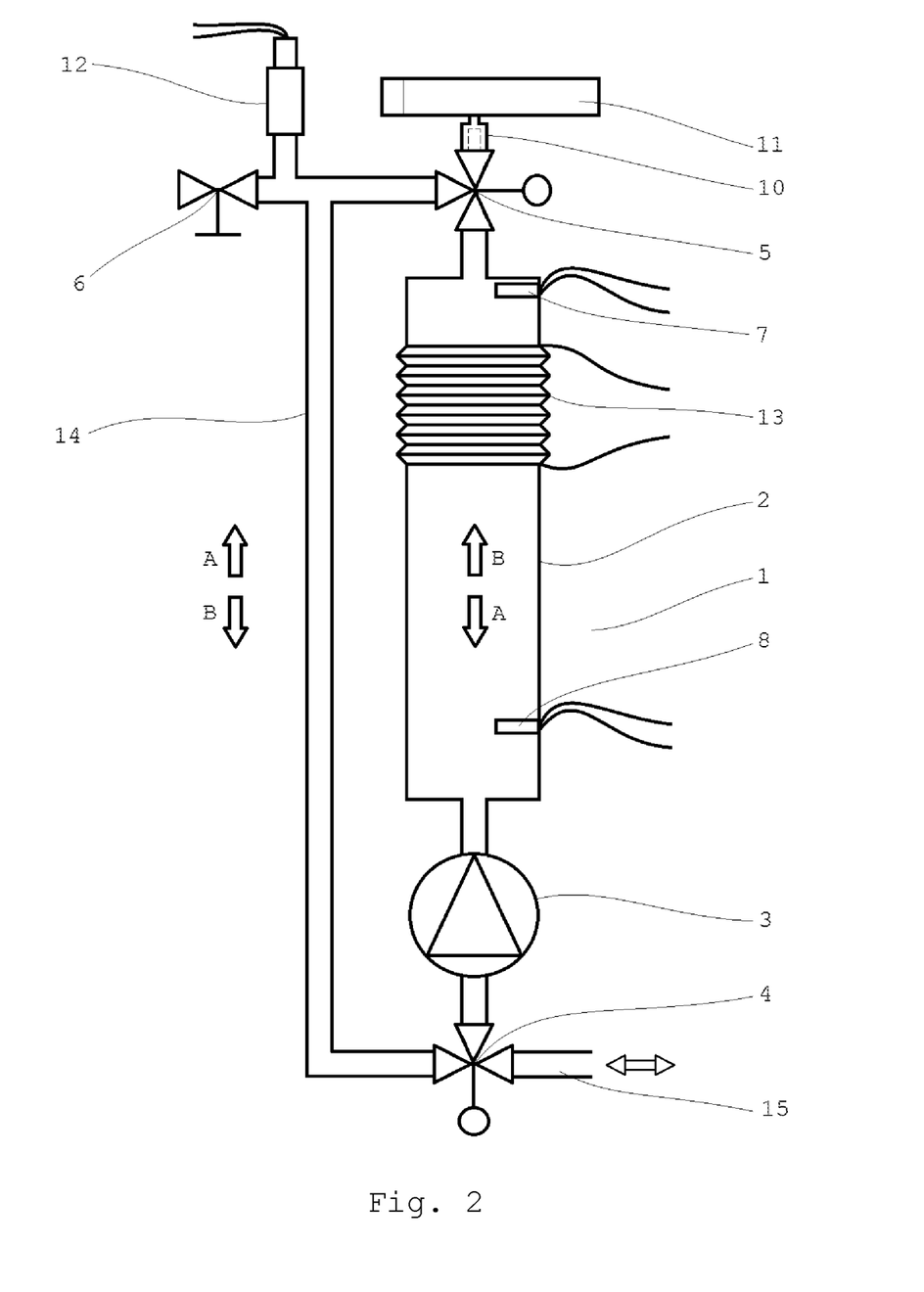
FIG. 2 illustrates a schematic view of a system according to a second embodiment of the present invention.

In FIG. 2 a schematic view of a system 1 according to a second embodiment of the present invention is illustrated. The system 1 includes a container 2, a liquid pump 3, a first three-way valve 4, a second three way valve 5, a valve 6, a first liquid level sensor 7, and a second liquid level sensor 8. The system 1 may be further equipped with an optional third liquid level sensor 9 which is not shown in FIG. 2. The system also includes a gas/liquid separation vessel 10, a measurement chamber 11, a pressure sensor 12, piping 14, and an inlet/outlet pipe 15. The system may also include a temperature sensor which is not shown in FIG. 2. The temperature sensor is typically arranged in the container 2.

Additionally, the container 2 of the system 1 includes a heater element 13 for acceleration of the dissolving process by heating the liquid in the container 2. According to other embodiments, a thermoelectric cooling element is used to cool the liquid depending on the temperature dependence of the dissolution coefficients of the gas components in the liquid. A further benefit of temperature control is that solubility coefficients remain constant, if the temperature is kept constant. This especially improves measurement repeatability.

Figure 3:
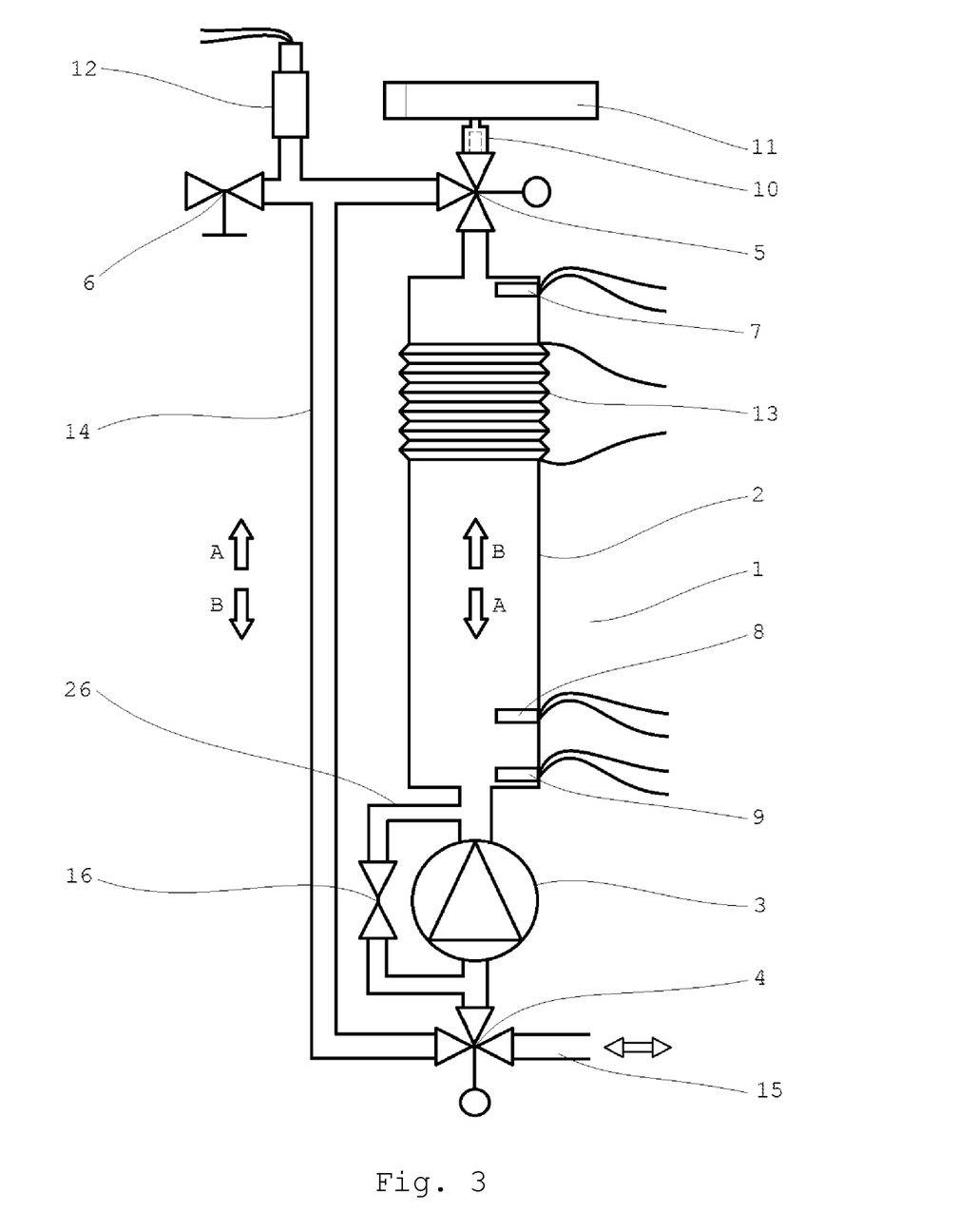
FIG. 3 illustrates a schematic view of a system according to a third embodiment of the present invention.

In FIG. 3 a schematic view of a system 1 according to a third embodiment of the present invention is illustrated. The system 1 includes a container 2, a two-way liquid pump 3, a first three-way valve 4, a second three way valve 5, a valve 6, liquid level sensors 7, 8, 9, a gas/liquid separation vessel 10, an measurement chamber 11, a pressure sensor 12, a heating element 13, piping 14, and an inlet/outlet pipe 15.

Additionally, the system 1 includes a bypass valve 16 and additional piping 26 in order to bypass the two-way pump 3. After the gas or gas mixture extraction rate has been slowed down and pressure increase saturated, the first three-way valve 4 is opened towards the inlet/outlet piping 15, the second three-way valve 5 is opened towards the measurement chamber 11. Then the bypass valve 16 is opened to let the liquid bypass the two-way liquid pump 3 in order to minimize gas extraction of the incoming liquid. Bypassing takes place by means of hydrostatic pressure. Contrary to using the liquid pump 3, there are no limits to the flow speed. Bypassing typically takes place with a mass flow which is less than the minimum mass flow to be created by the liquid pump 3. A laminar flow without any turbulence may be incurred depending on the flow speed. The raising oil level pushes the extracted gas or gas mixture sample to the measurement chamber 11. Bypassing is typically stopped when the liquid level reaches the first liquid level sensor 7. The second three-way valve 5 is then closed towards the measurement chamber and the IR transmittance measurement is performed. The additional bypass piping 26 is sufficiently long and has a cross sectional area selected such that a high flow resistance is provided. According to a certain embodiment, the cross sectional area of the bypass piping 26 is the system's smallest piping cross sectional area.

According to another embodiment, the bypassing can be optionally terminated after, for example, 50% of the container 2 has been filled with oil and the remaining amount can be transferred by slow speed pumping of oil into the container 2 until the liquid level reaches the first liquid level sensor 7. In this case, the liquid speed in the tubing may be, for example, less than 0.2 [m/s]. During the bypassing, the pressure has increased and thus the risk for undesired gas formation has diminished. Advantageously the oil inlet speed during bypassing is slower than the minimum pumping speed, and furthermore the fluid flow is more laminar, thus reducing unwanted gas formation.

Figure 4:
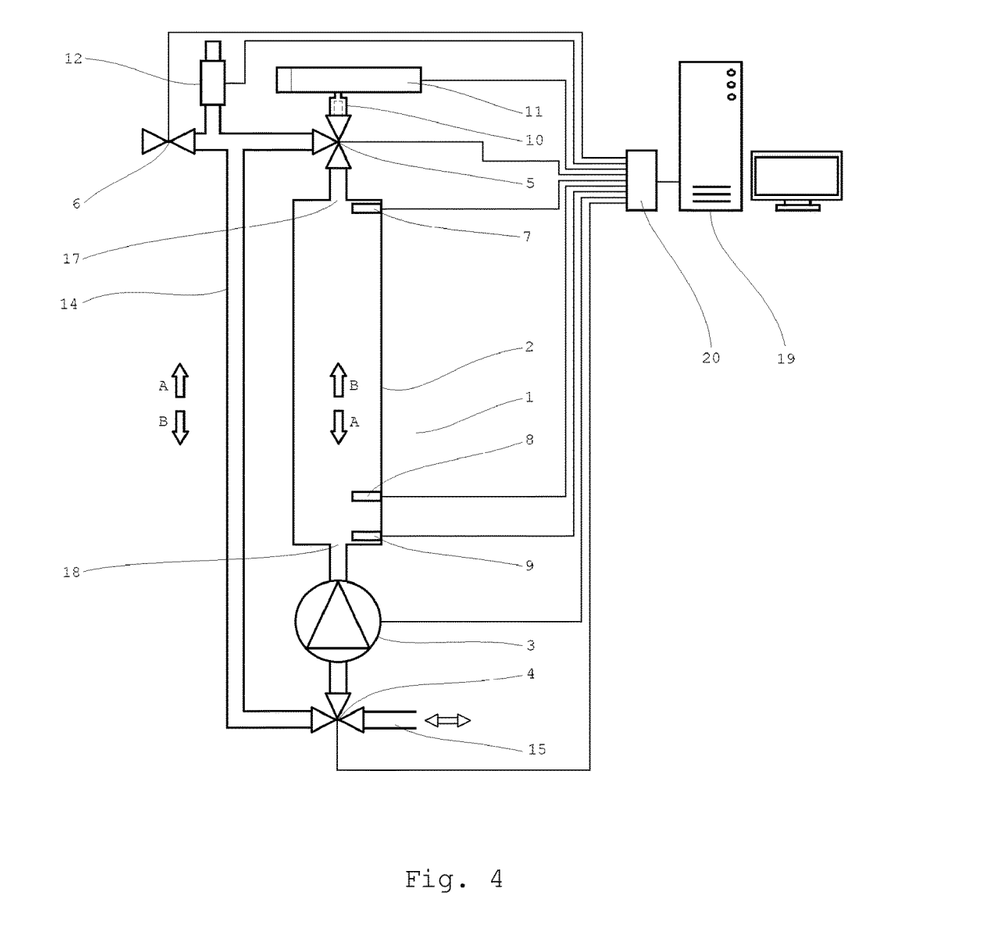
FIG. 4 illustrates a schematic view of a system according to a fourth embodiment of the present invention.

In FIG. 4 a schematic view of a system 1 according to a fourth embodiment of the present invention is illustrated. The system 1 for extracting gas or gas mixtures from a liquid for performing dissolved gas or gas mixture analysis includes a container 2 for storing a liquid and/or a gas or gas mixture, a liquid pump 3 which is connected to the container 2, a means for feeding the system 1 with a liquid and emptying the system 1 of the liquid, a gas analyzer which is connected to the container 2, and a piping 14 which is connected to the container 2, and wherein the piping 14, the liquid pump 3 and the container 2 are configured to circulate the liquid. The system 1 further includes liquid level sensors 7, 8, 9, valves 4, 5, 6, and a pressure sensor 12.

Additionally, the system 1 comprises a computerized device 19 which includes a computer readable medium having stored thereon a set of computer implementable instructions capable of causing a processor, in connection with the system 1, to calculate a gas or gas mixture content dissolved in a liquid sample. The first three-way valve 4, the liquid pump 3, the first liquid level sensor 7, the second liquid level sensor 8, the third liquid level sensor 9, the second three-way valve 5, the gas analyzer, the valve 6, and the pressure sensor 12 are electronically connected to the computerized device 19 via an analogue/digital converter 20. The system 1 may further comprise a relay unit, which is not shown in FIG. 4, for controlling the three-way valves 4, 5.

The automated system 1 is configured such that parameters of the system are continuously or step-wise controlled and/or monitored. The parameters may be, for example, status of each of the valves 4, 5, 6 (open/closed), direction of the liquid pump 3 (A, B), pumping speed, status of liquid level sensors 7, 8, 9, and pressure in the container 2 and/or the measurement chamber 11 of the gas analyzer.

The computerized device can also be used for zero signal generation by mathematical extrapolation of a first and second signal $S_1$, $S_2$ to zero pressure $P_0$ and/or for subtraction of the offset of the zero signal $S_0$ from the offsets of the first and second signal $S_1$, $S_2$.

Additionally, the computerized device may be, for example, also be used for storing measurement data such as name or number of the liquid sample, temperature of the liquid sample, volume of the liquid sample, pressure in the measurement chamber 11, pressure in the container 2, first pressure $P_1$, second pressure $P_2$, zero pressure $P_0$, intensity data as a function of wavelength, radiant source data, Fabry-Perot interferometer data, detector data, and/or signals $S_1$, $S_2$ as a function of wavelengths.

Figure 5:
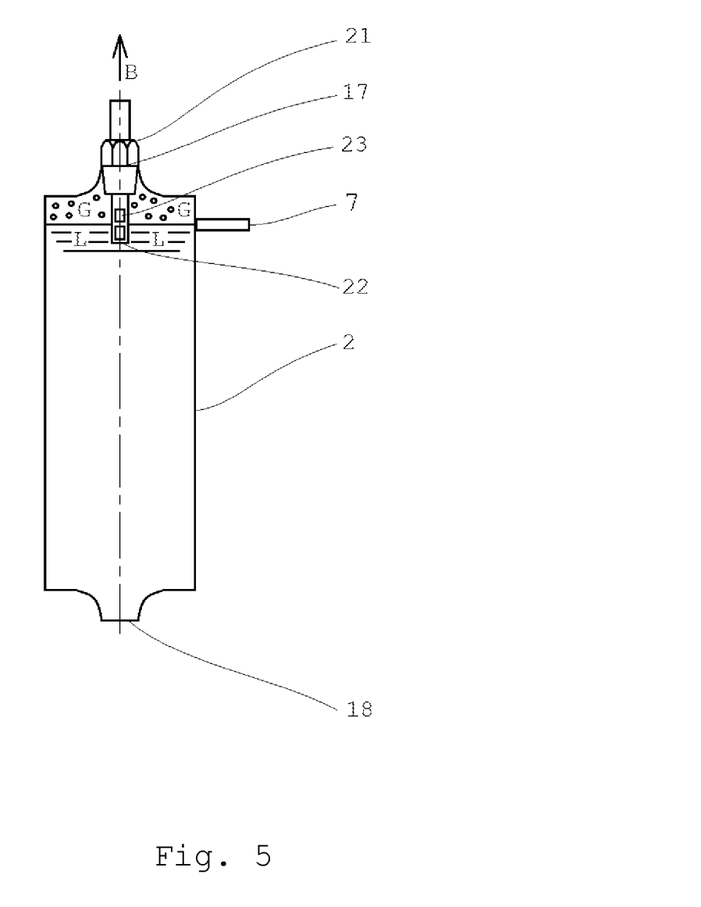
FIG. 5 illustrates a schematic view of a container of a system according to a fifth embodiment of the present invention.

In FIG. 5 a schematic view of a container of a system 1 according to a fifth embodiment of the present invention is illustrated. According to the embodiment, the container 2 is not fully filled with liquid until overpressure is shown. In this case, the liquid level only reaches the first liquid level sensor 7. A small amount of gas or gas mixture G remains above the liquid L. The container 2 is connected to the piping 14, which is not shown in FIG. 5, via a plug 21 which is inserted in the first opening 17 of the container 2. The plug 21 represents a suction member. The connection between the container 2 and the piping 14 is hermetically sealed by means of the plug 21. The plug 21 includes a fluid channel and a nozzle which protrudes into the container 2. The nozzle 22 further includes holes 23. Some of the holes 23 of the nozzle 22 are arranged under a surface of the liquid L. The remaining holes are arranged above the surface of the liquid L. The liquid L is pumped in the direction of arrow B during the dissolving phase of the system 1. The gas or gas mixture G in the container 2 can be sucked through the holes 23 of the nozzle 22 in the direction of arrow B while liquid L is sucked through holes 23 of the nozzle 22 which are arranged under the surface of the liquid L, i.e. both gas or gas mixture G and liquid L can be simultaneously sucked into the suction member, if the liquid surface is near the suction member. Said suction member may be, for example, a perforated tube having a blocked end. The gas or gas mixture G can be dissolved in the liquid L during circulation in the system 1. The gas or gas mixture G in the container 2 above the liquid L reduces the risk of cavitation during pumping of the liquid L.

Figure 6:
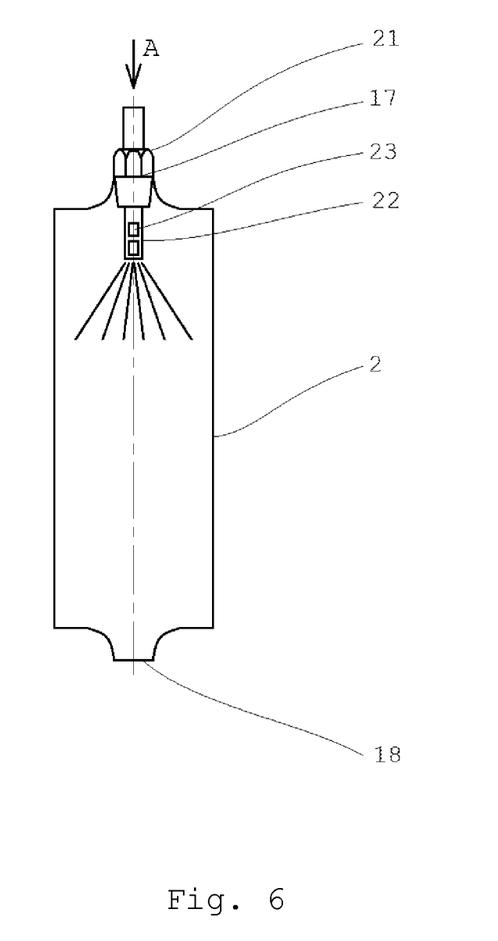
FIG. 6 illustrates a schematic view of a container of a system according to a sixth embodiment of the present invention.

In FIG. 6 a schematic view of a container of a system 1 according to a sixth embodiment of the present invention is illustrated. The container 2 is connected to the piping 14, which is not shown in FIG. 6, via a plug 21 which is inserted in the first opening 17 of the container 2. The connection between the container 2 and the piping 14 is hermetically sealed by means of the plug 21. The plug 21 includes a fluid channel and a nozzle 22 which protrudes into the container 2. The liquid sample is pumped in the direction of arrow A with high speed during the extraction phase of the system 1. The velocity of the liquid typically increases in the nozzle 22 due to the cross sectional area of the nozzle 22 which is normally less than the cross sectional area of the piping 14. The nozzle 23 is configured such that the liquid sample is sprayed into the container 2, thus improving the gas or gas mixture extraction from the liquid sample.

Figure 7:
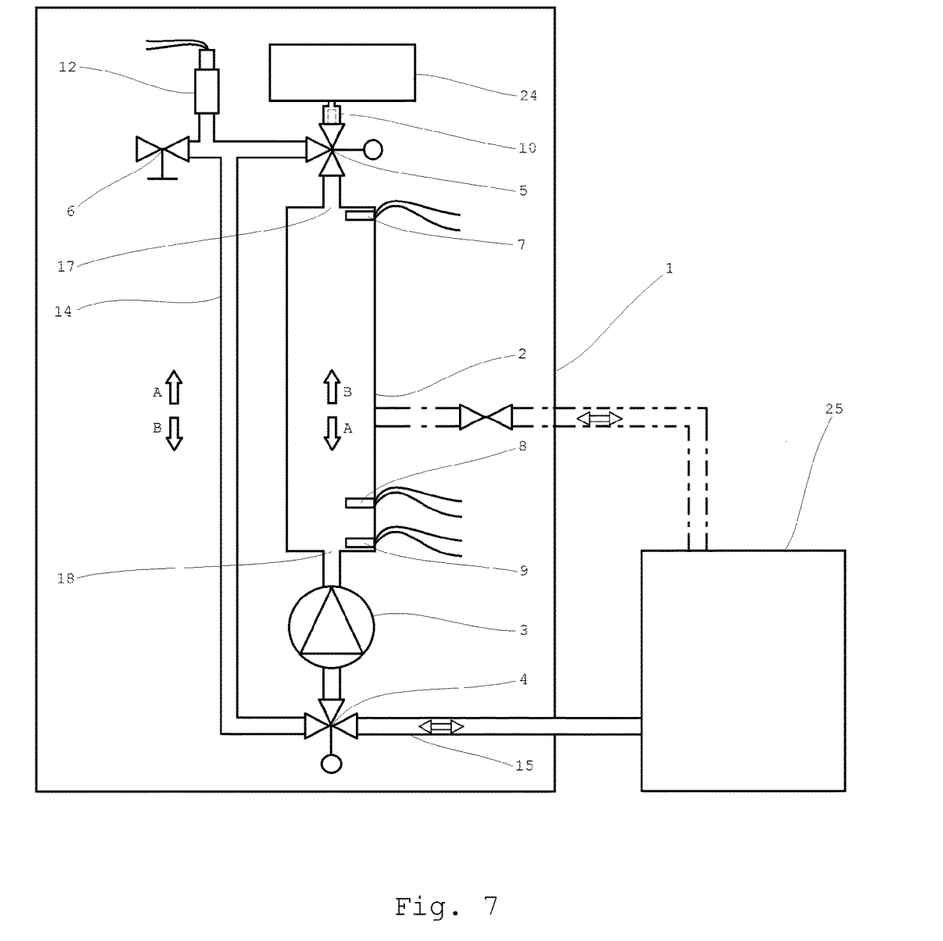
FIG. 7 illustrates a schematic view of a system according to a seventh embodiment of the present invention, which is connected to an electric power transformer.

In FIG. 7 a schematic view of a system 1 according to a seventh embodiment of the present invention is illustrated. The system 1 is connected to an electric power transformer 25 by means of the inlet/outlet piping 15. The system 1 is attached to the power transformer 25 only using the inlet/outlet piping 15. An additional mounting bracket or long piping is not required. The oil contained in the electric power transformer 25 represents the liquid source. The system 1 is configured to extract a gas or gas mixture from a liquid sample of the liquid source utilizing mechanical agitation and pressure reduced from ambient air. The system 1 is further configured to pressurize the extracted gas or gas mixture into a gas analyzer 24 and to subsequently perform dissolved gas or gas mixture analysis by means of the gas analyzer 24. The gas analyzer 24 may be, for example, based on an IR transmittance measurement technique, a photo acoustic measurement technique, or any other measurement technique. Furthermore, the system 1 is configured to dissolve the extracted gas or gas mixture back into the liquid sample and to conduct the liquid sample back into the electric power transformer 25. According to a certain embodiment, the electric power transformer 25 is connected to the container 2 via an additional inlet/outlet piping which is shown in FIG. 7 by dotted lines. The additional inlet/outlet piping also includes a valve.

Figure 8:
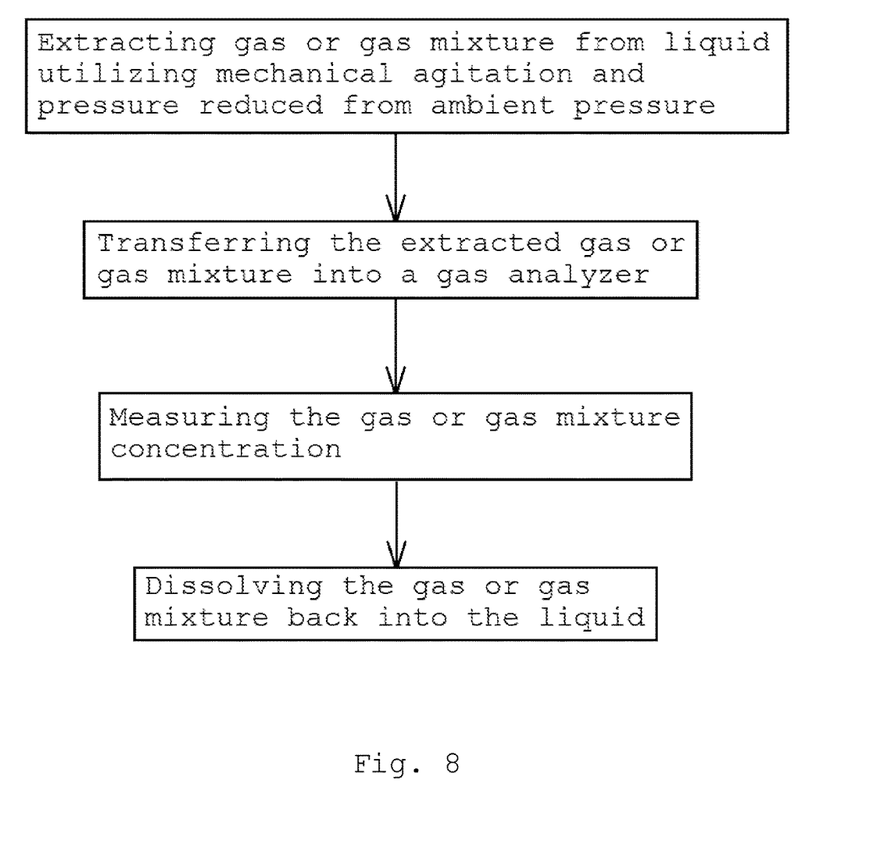
FIG. 8 illustrates a flow chart of method steps according to an embodiment of the present invention.

In FIG. 8 a flow chart of method steps according to an embodiment of the present invention is illustrated. A gas or gas mixture is extracted from a liquid sample utilizing mechanical agitation and pressure reduced from ambient air pressure. The extracted gas or gas mixture is then transferred into a gas analyzer by means of elevating a liquid surface. The measurement technique may be, for example, a photo acoustic measurement method. After measurement of the gas or gas mixture concentration the gas or gas mixture is dissolved back into the liquid.

Figure 9:
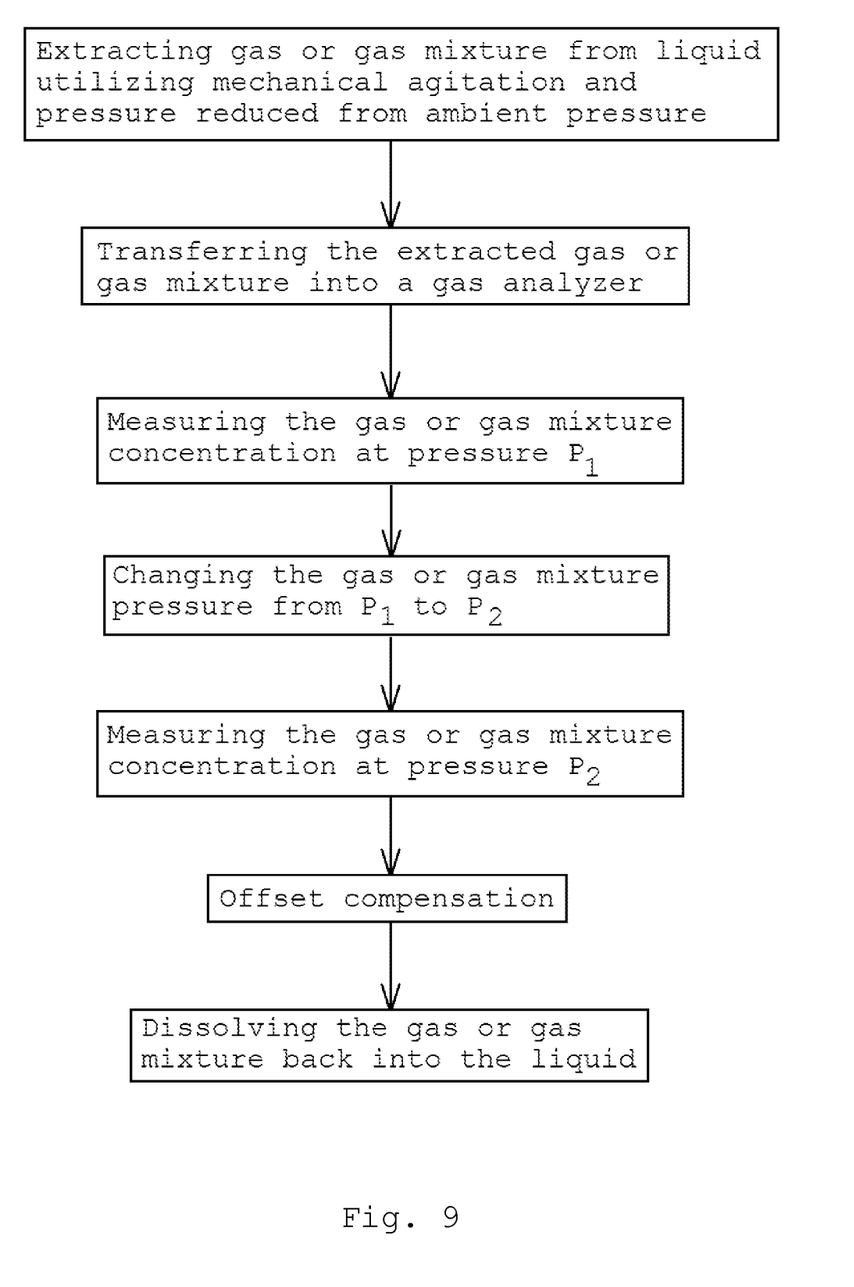
FIG. 9 illustrates a flow chart of method steps according to another embodiment of the present invention.

In FIG. 9 a flow chart of method steps according to an embodiment of the present invention is illustrated. First, a gas or a gas mixture is extracted from a liquid sample utilizing mechanical agitation and pressure reduced from ambient air pressure. Secondly, the extracted gas or gas mixture is transferred into a gas analyzer by means of elevating a liquid surface. The raising liquid level pushes the extracted gas or gas mixture sample into a measurement chamber 11, for example an IR gas measurement chamber, of a gas analyzer.

Then a first gas or gas mixture concentration measurement takes place at a first pressure $P_1$. The measurement may, for example, comprise the following steps: 1. A measurement signal is generated by means of a radiant source. 2. The measurement signal is directed to a measurement object in the measurement chamber containing the gas or gas mixture to be measured. 3. The measurement signal is modified by a filter or a wavelength dispersive element in order to enable the observation of the wavelength dependence of the signal intensity. 4. The modified signal is detected by means of a detector or a detector matrix.

The filtering of the measurement signals may be implemented by means of an electrically tunable, short-resonator Fabry-Perot interferometer or the wavelength dispersion of the measurement signals may be implemented by means of a grating. The signal $S_1$ as a function of the wavelength A may be measured at at least two wavelengths $A_1$, $A_2$ at the first pressure $P_1$.

Subsequently, the pressure in the measurement chamber is varied from the first pressure $P_1$ to a second pressure $P_2$. The gas pressure or gas mixture pressure is varied by elevating or lowering the liquid surface. In other words, the pressure in the measurement chamber 11 may be increased by raising a liquid level or decreased by lowering a liquid level. Surprisingly, the pressure can be varied by changing the liquid level without generating too much gas exchange between the liquid/gas phases. The gas exchange between the phases is very slow unless the liquid is disturbed by an additional mechanical agitation, which can speed up the exchange rate drastically. Then signal measurements at the second pressure $P_2$ or at several different pressures may be performed. The signal $S_2$ as a function of the wavelength is measured at at least two wavelengths $\lambda_1$, $\lambda_2$ at the second pressure $P_2$. The wavelengths $\lambda_1$, $\lambda_2$ used at the second pressure $P_2$ are essentially or exactly the same as at the first pressure $P_1$.

Subsequently, the signal $S_0$ may be generated by mathematical extrapolation the signal to zero pressure $P_0=0$ [bar], and then the offset $S_0$ is subtracted from the signals $S_1$ and $S_2$. According to another embodiment, the offset $S(P_1)-S(P_0)$ may also be determined by the approximation $S(P_1)-S(P_0)=(S(P_1)-S(P_2))*(P_1-P_0)/(P_1-P_2)$.

Finally, the gas or gas mixture is dissolved back into the liquid by transferring the gas or gas mixture out of the measurement chamber 11, closing the second three-way valve 5 towards the measurement chamber 11, feeding liquid into the system 1 until overpressure, and circulating the liquid until the gas or gas mixture present in the system 1 is dissolved into the liquid and pressure is lowered. The extracted gas or gas mixture is dissolved after measurement into the liquid such that the chemical content of the liquid remains intact and the liquid contains no gas bubbles when returned to the system under measurement, i.e. the liquid source.

The liquid can be further transferred out of the system 1 and another liquid sample can be transferred into the system 1 in order to start a new extraction/measurement cycle.

Although the present invention has been described in detail for the purpose of illustration, various changes and modifications can be made within the scope of the claims. In addition, it is to be understood that the present disclosure contemplates that, to the extent possible, one or more features of any embodiment may be combined with one or more features of any other embodiment.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to one embodiment or an embodiment means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment. Where reference is made to a numerical value using a term such as, for example, about or substantially, the exact numerical value is also disclosed.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

In the following description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The verbs "to comprise" and "to include" are used in this document as open limitations that neither exclude nor require the existence of also un-recited features. The features recited in depending claims are mutually freely combinable unless otherwise explicitly stated. Furthermore, it is to be understood that the use of "a" or "an", that is, a singular form, throughout this document does not exclude a plurality.

The gas analyzer is typically an IR gas analyzer. The invention is in particular not limited to IR gas analyzers. The invention is further not limited to be used for on-line measurements of gas or gas mixtures dissolved in oil contained by electric power transformers and their load tap changers. The invention may be also used for other applications.

In general, the vertical direction is defined as being perpendicular to a horizontal direction and a transversal direction. The horizontal direction is further defined as being perpendicular to the transversal direction. A rotation of one of the aforementioned directions about at least one axis of rotation leads to a rotation of the other two directions about the at least one axis of rotation within the meaning of the detailed description of embodiments described above.

LIST OF REFERENCE NUMBERS 1 system
2 container
3 two-way liquid pump
4 first three-way valve
5 second three-way valve
6 valve
7 first liquid level sensor
8 second liquid level sensor
9 third liquid level sensor
10 gas/liquid separation vessel
11 measurement chamber
12 pressure sensor
13 heater element
14 piping
15 inlet/outlet piping
16 bypass valve
17 first opening
18 second opening
19 computerized device
20 analogue/digital converter
21 plug, gas/liquid inlet member
22 nozzle
23 hole
24 gas analyzer
25 power transformer
26 bypass piping
A first liquid flow direction
B second liquid flow direction
G gas or gas mixture
L liquid
$P_0$ zero pressure
$P_1$ first pressure
$P_2$ second pressure
$S_0$ zero signal
$S_1$ first signal
$S_2$ second signal
$\lambda$ wavelength
$\lambda_1$ first wavelength
$\lambda_2$ second wavelength

The invention claimed is:

1. A system for extracting gas from a liquid for performing dissolved gas analysis, the system comprising:
    a container for storing at least one of a liquid and a gas,
    a bidirectional liquid pump which is connected to the container,
    a piping which is connected to the container and the bidirectional liquid pump, and wherein the system is configured to extract the gas from the liquid by circulating the liquid with the bidirectional liquid pump in a first direction along a closed flow channel formed by the piping, the bidirectional liquid pump, and the container, and
    wherein the system is configured to dissolve the gas back into the liquid by circulating the liquid with the bidirectional pump in a second direction different than the first direction along the closed flow channel formed by the piping, the bidirectional liquid pump, and the container.

2. The system according to claim 1, wherein the bidirectional liquid pump is configured to reverse a liquid flow direction or the system comprises a means for reversing the liquid flow direction.

3. The system according to claim 1, wherein the system includes a pressure sensor which is connected to the container, the piping, and/or a measurement chamber of the gas analyzer.

4. The system according to claim 1, wherein the system includes means for measuring a liquid level in the container.

5. The system according to claim 1, wherein the means for feeding the system with a liquid and emptying the system of the liquid comprises an inlet/outlet piping.

6. The system according to claim 5, wherein the inlet/outlet piping is connected to a first three-way valve which is connected to the liquid pump and the piping.

7. The system according to claim 6, wherein the system includes a second three-way valve which is connected to the container, the piping and the gas analyzer.

8. The system according to claim 1, wherein the system includes a valve configured to remove air out of the system.

9. The system according to claim 1, wherein the container includes a first opening essentially on top of the container and a second opening essentially at the bottom of the container.

10. The system according to claim 1, wherein the liquid pump is hermetically sealed.

11. The system according to claim 1, wherein a gas/liquid inlet member on top of the container is configured to simultaneously suck in both gas and liquid.

12. The system according to claim 11, wherein the cross sectional area of the gas/liquid inlet member is less than 50% of the cross sectional area of the piping connected to the gas/liquid inlet member.

13. The system according to claim 1, wherein the system comprises a device for stirring the liquid mechanically.

14. The system according to claim 1, wherein the system comprises a means for controlling the temperature of the liquid in the container.

15. A non-transitory computer readable medium having stored thereon a set of computer implementable instructions capable of causing a processor, in connection with the system according to claim 1, to calculate a gas or gas mixture content dissolved in a liquid sample.

* * * * *